United States Patent
DeLaRama et al.

[11] Patent Number: 5,381,782
[45] Date of Patent: Jan. 17, 1995

[54] BI-DIRECTIONAL AND MULTI-DIRECTIONAL MINISCOPES

[75] Inventors: Alan DeLaRama, Cerritos; Larry A. Dial, Chino Hills; Richard J. Harp, Carlsbad; Thomas L. Hursman, Diamond Bar; Alfred S. Soria, Corona Del Mar; R. J. Serra, Irvine; Steve Tarpening, Oceanside, all of Calif.

[73] Assignee: Spectrum Medsystems Corporation, Diamond Bar, Calif.

[21] Appl. No.: 21,955

[22] Filed: Feb. 23, 1993

Related U.S. Application Data

[63] Continuation of Ser. No. 818,670, Jan. 9, 1992, abandoned.

[51] Int. Cl.$^6$ .............................................. A61B 1/00
[52] U.S. Cl. ............................................ 128/4; 604/95; 138/118
[58] Field of Search ............... 604/95, 280, 281, 282; 128/4, 6; 138/118, 103, DIG. 8

[56] References Cited

U.S. PATENT DOCUMENTS

| | | | |
|---|---|---|---|
| 3,162,214 | 12/1964 | Bazinet. | |
| 3,946,727 | 3/1976 | Okada et al. | |
| 3,948,251 | 4/1976 | Hosono. | |
| 4,290,421 | 9/1981 | Siegmund | 128/6 |
| 4,580,551 | 4/1986 | Siegmund et al. | 128/4 |
| 4,686,963 | 8/1987 | Cohen. | |
| 4,805,595 | 2/1989 | Kambara. | |
| 4,805,596 | 2/1989 | Hatori. | |
| 4,819,634 | 4/1989 | Shiber | 604/95 X |
| 4,899,787 | 2/1990 | Ouchi. | |
| 4,998,923 | 3/1991 | Samson et al. | 604/95 X |
| 5,002,041 | 3/1991 | Chikama. | |
| 5,058,568 | 10/1991 | Irion. | |
| 5,106,381 | 4/1992 | Chikama. | |
| 5,195,968 | 3/1993 | Lundquist et al. | 604/95 |
| 5,235,964 | 8/1993 | Abenaim | 128/4 |

FOREIGN PATENT DOCUMENTS

| | | |
|---|---|---|
| 8816621924 | 5/2982 | Japan. |
| WO90/10417 | 9/1990 | WIPO. |

OTHER PUBLICATIONS

Karl Storz Ureteropyeloscope, Karl Storz Endoscopy-America, Inc., 10111 W. Jefferson Boulevard, Culver City, Calif. 90232 3578.
Biliary Tract Endoscopy, Intramed Laboratoriesk, Inc., 11100 Roselle Street, San Diego, Calif. 92121.
APN-2 Flexible Choldeochoscope, Circon, ACMI, P.O. Box 1971 Stamford, Conn. 06904-1971.
APN-3 Flexible Choledochoscope, Circon, ACMI, P.O. Box 1971 Stamford, Conn. 06904-1971.
AUR-9 Flexible Ureteropyeloscope, Circon, ACMI, P.O.Box 1971, Stamford, Conn. 06904-1971.

*Primary Examiner*—Richard J. Apley
*Assistant Examiner*—Karen A. Jalbert
*Attorney, Agent, or Firm*—Stetina Brunda & Buyan

[57] ABSTRACT

A bi-directional endoscope comprising a catheter body having a tubular spring frame attached to and extending axially from the distal end thereof. The spring frame comprises a spring body which includes a tip member positioned on the distal end thereof, and a plurality of relief slots disposed therein for allowing the deflection of the spring frame within a first deflection plane. The relief slots are formed in the spring body in a manner defining first and second longitudinally extending stiffening portions which are oriented substantially diametrically opposite each other therewithin. Extending longitudinally through the catheter body and spring frame is a pair of activation wires which are encased by a pair of support sleeves. The spring frame is deflected by stressing the activation wires by subjecting either of the wires to a tensile force. Stressing the wires as operable to transmit the tensile force from the stressed wire to the tip member thus causing the spring body to deflect in the first deflection plane toward the stressed wire.

12 Claims, 3 Drawing Sheets

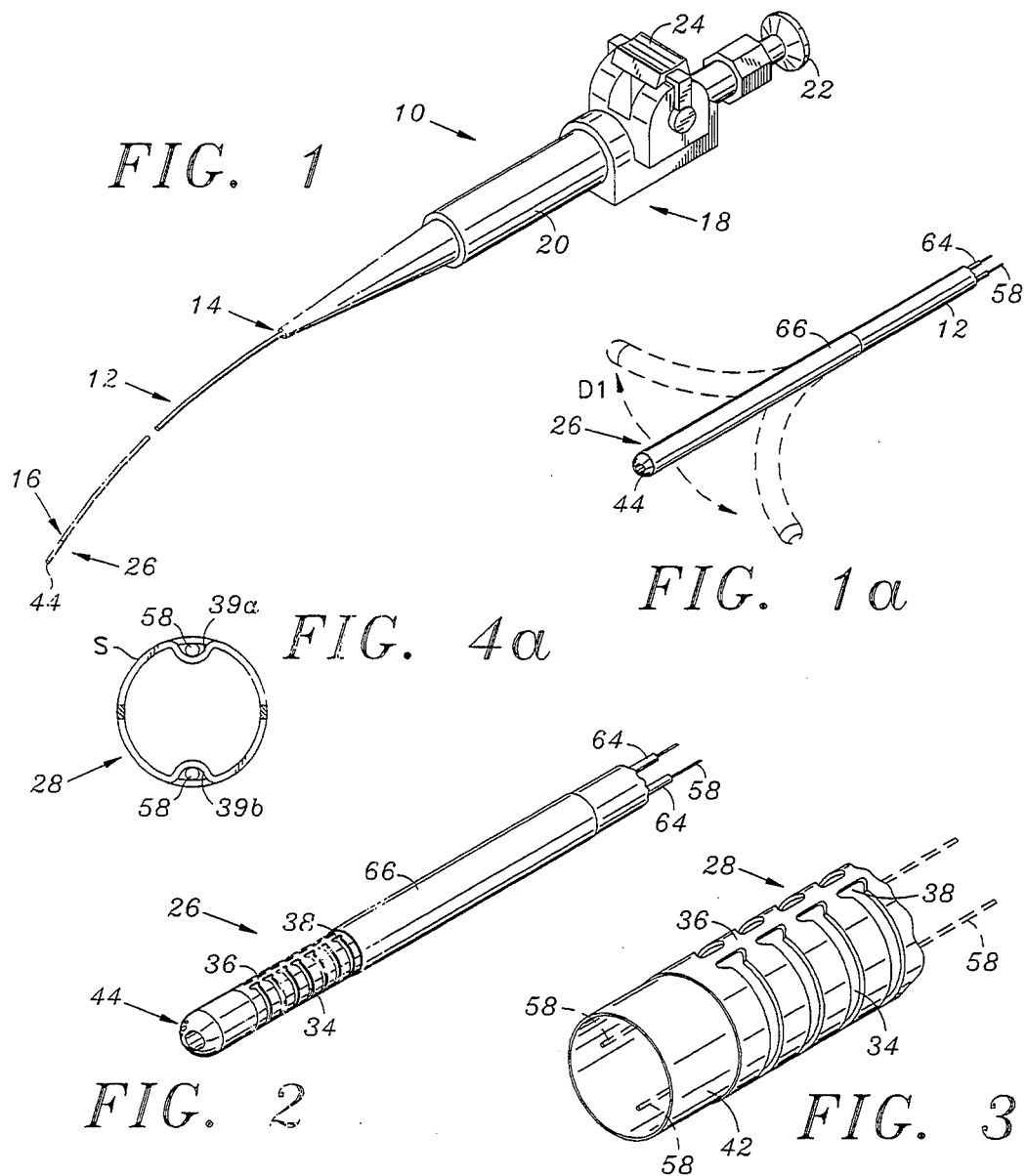

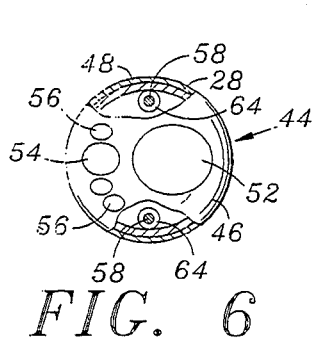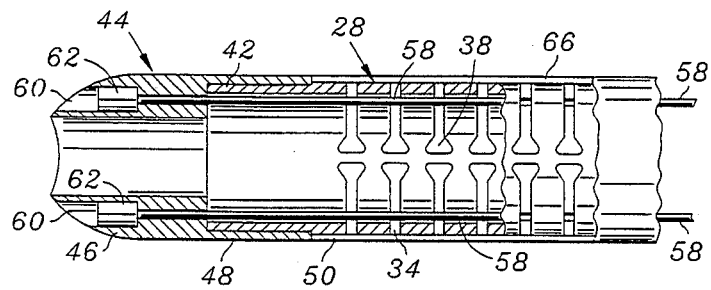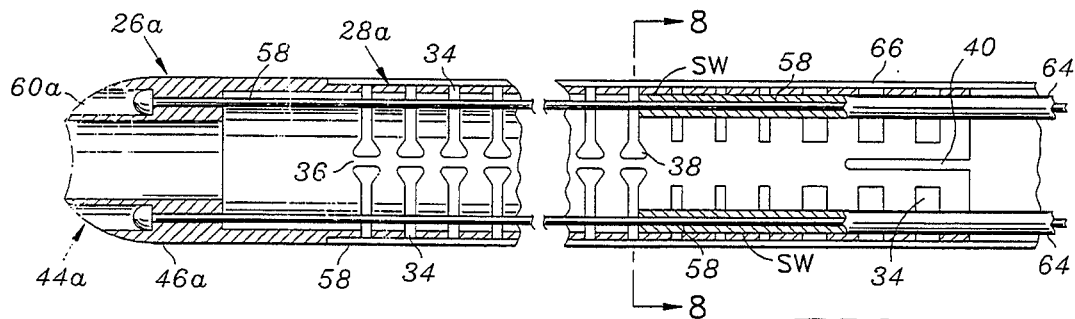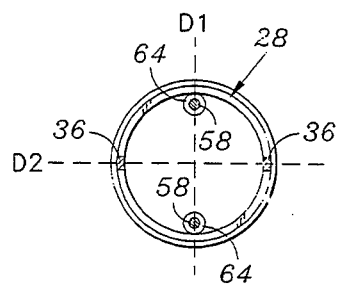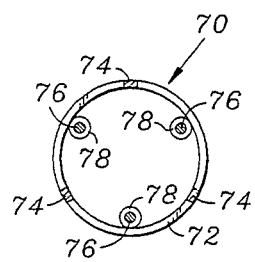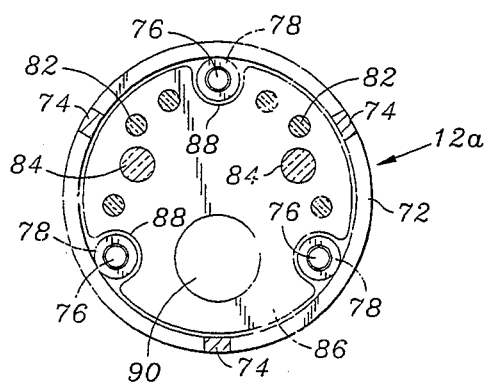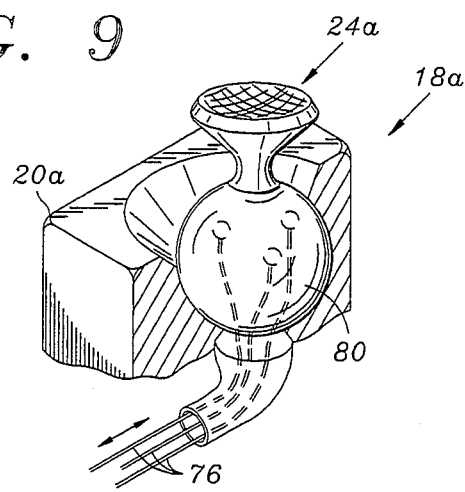

BI-DIRECTIONAL AND MULTI-DIRECTIONAL MINISCOPES

RELATED APPLICATIONS

The present application is a continuation-in-part of U.S. patent application Ser. No. 07/818,670, filed Jan. 9, 1992, now abandoned, entitled BI-DIRECTIONAL MINISCOPE, the disclosure of which is incorporated herein by reference.

FIELD OF THE INVENTION

The present invention relates generally to medical equipment and more particularly to endoscopes which are capable of being guided or steered in two (2) or more directions.

BACKGROUND OF THE INVENTION

Endoscopes are widely used in many medical procedures for viewing otherwise inaccessible areas of bodily organs, cavities, passageways, etc. Generally, endoscopes include an elongate catheter body, or similar structure wherein optical fibers are arranged both for transmitting illumination to the distal end of the catheter body to illuminate a viewing field, and for carrying the optical image back to the physician. One or more lenses may be positioned on the distal end of the endoscope to focus the optical image received by, or the illumination cast by the instrument.

In many applications it is desirable that the catheter portion of the endoscope be "steerable", bendable or maneuverable from the proximal end of the scope to facilitate guidance of the catheter portion through tortuous or furcated anatomical passageways. Additionally, the ability to bend the catheter portion of the scope at or near its distal end may enable the operator to visually scan an expanded viewing area by bending or otherwise manipulating the distal end of the scope. Indeed, in many applications it is desirable that the distal end of the scope be capable of undergoing a full 180° or more of deflection so that the operator may "look back" at a site behind or proximal to the distal end of the scope. Such "retro-viewing" is often desirable, for example, when examining the puncture site of a gallbladder during a procedure. Second, the ability to maneuver the tip makes it easier to guide the tip of the endoscope properly through the often highly branched and convoluted passageways near organs such as the coronary arteries of the heart or the branched ducts of the biliary tree.

There are accordingly a large number of endoscopes now available. The following patents show examples of existing devices and methods for manufacturing maneuverable catheters, endoscopes, and the like:

| No. | Inventor(s) | Issue Date |
| --- | --- | --- |
| 4,934,340 | Ebling et al. | June 19, 1990 |
| 4,911,148 | Sosnowski et al. | March 27, 1990 |
| 4,899,732 | Cohen | February 13, 1990 |
| 4,669,172 | Petruzzi | June 2, 1987 |
| 4,418,688 | Loeb | December 6, 1983 |
| 3,998,216 | Hosono | December 21, 1976 |
| 3,946,727 | Okada et al. | March 30, 1976 |
| 3,739,770 | Mori | June 19, 1973 |
| 3,572,325 | S. Bazell et al. | March 23, 1971 |
| 3,610,231 | Nagashige Takahashi | October 5, 1971 |
| 3,521,620 | W. A. Cook | July 28, 1970 |

Similar devices are disclosed in the following non-U.S. texts:

U.K. Patent Application No. GB 2 130 885 A (F. A. Coulston-Iles, published Jun. 13, 1984);

U. K. Patent Specification No. 1 208 639 (Cook, published Oct. 14, 1970);

European Patent Application No. 253 687 (Millar et al., published Jan. 20, 1988); and European Patent No. EP 370 785, (issued to Medical Institute, Inc., May 30, 1990).

In order to control the deflection of the distal tip of an endoscope, many designs incorporate one or more activation wires that run the length of the endoscope. These are attached to the distal tip, which often is in the form of a stack of hollow rings which are attached to each other and allow pivoting of each ring relative to its neighbor. By pulling on an activation wire, the distal end deflects towards the wire.

The designer of wire-activated endoscopes is faced with several conflicting requirements. The diameter of the endoscope should be as small as possible so that the endoscope can be maneuvered into the smallest possible passageways and cavities. On the other hand, the outer casing of the endoscope should be as strong as possible to avoid breaking, kinking, and buckling. It should also be stiff to promote the accurate and predictable transmission of torque. At the same time, the activation wire must be able to withstand the tensile load required to deflect the distal end of the endoscope. If, however, the endoscope has either thick outer walls or a mainly solid cross-section, its bending moment will increase and require the activation wire to bear and transmit even greater force in order to deflect the tip. Also, a stiff endoscope will not easily traverse tortuous tracts. Additionally, small-diameter endoscopes have a small moment arm for the activation wire, so that the activation wire must transmit greater force to achieve a given moment.

In order to decrease the diameter of the endoscope, activation wires, if such are even provided, are typically unprotected and are usually welded or soldered directly to the outer casing of the instrument. This arrangement, however, decreases the tensile strength of the wires and reduces the bending force they can bear and transmit to the tip. It also increases the risk of buckling not only of the outer casing, but also of the activation mechanism itself. An additional disadvantage of thick-walled designs, or designs having mostly solid cross-section, is that the area left over for carrying illumination and optical fibers, working lumens, etc., is correspondingly decreased.

Additional typical disadvantages of many existing endoscope designs are that they bend only in one direction (which means that the entire scope must be rotated in order to see in the other direction), and that they are often difficult to manufacture. Furthermore, existing designs that incorporate activation wires typically join these wires to the outer casing of the scope using methods such as soldering or welding that either weaken the wires themselves or decrease the force they are able to bear and transmit.

One object of this invention is therefore to provide an endoscope or "miniscope" that is simple to build, rugged and compact, that avoids the problem of buckling, that has a small outer diameter, and that provides full tip deflection using activation wires that are mounted and joined in such a way that they are able to transfer relatively large activation forces securely.

SUMMARY OF THE INVENTION

The present invention comprises an elongate, bendable catheter of the type broadly applicable to numerous medical applications wherein it is desirable to insert a catheter into a tubular anatomical structure or passageway. The catheter device of the present invention may be incorporated as part of an endoscope insertable into a body cavity or passageway and utilizable to endoscopically view anatomical structures within the body. The bending capability of the catheter device of the present invention is provided by a tubular spring frame mounted on or formed on the catheter body, preferably near its distal end. The tubular spring frame has a series of individual slots or slits cut into the body of the tubular spring frame so as to render the tubular spring frame bendable in at least one direction. Preferably, two or more series of slots are formed in the tubular spring frame to render it bendable in two or more separate directions. The slots are preferably provided with strain relief end cut-outs having large radii to reduce metal fatigue and the potential of cracking the spring frame during repeated deflections. The proportions of the tubular spring frame wall thickness to the remaining web left between the strain relief end cut-outs determine the performance of the spring frame to act like a bendable spring without fatigue cracking, but with adequate columnal stiffness and spring return. At least one slotted segment of the tubular spring frame is provided with two (2) separate indentations, webs or wire engaging guide members located at opposite sides of the segment and configured to permit the control wires to pass therethrough and thereby providing support and guidance for each control wire to permit said control wires from engaging or tangling with one another during slackened periods. The control wires remain freely or slideably advanceable and retractable through such indentations, webs or wire guide members, while being laterally retained thereby. Each control wire is attached to a point on the tubular spring frame at or near its distal end such that retraction of said control wire will cause a series of the slits or slots formed in the tubular spring frame to close or compact, thus allowing the spring frame to bend in a lateral direction. The spring frame may be biased to a straight, non-bent configuration such that relief of the proximally directed tension on said control wire will permit the spring frame to return to a straight, non-bent configuration.

Two or more separate series of strain relief slots may be formed adjacent one another on opposite or different sides of the tubular spring body to permit deflection or bending of the tubular spring body in multiple directions or even 360° pivotal movement of the spring body about its longitudinal axis.

A control apparatus such as a bi-directional lever or a multi-directional lever in the nature of a joy stick may be positioned on the proximal end of the catheter body or endoscope and attached to the proximal end(s) of the control wire(s) so as to effect the desired bending or pivoting of the tubular spring member at desired times.

In accordance with a first alternative embodiment of the present invention, there is provided a bi-directional endoscope generally comprising an elongate, tubular catheter body having proximal and distal ends. Attached to and extending axially from the distal end of the catheter body is a generally cylindrical, tubular spring frame. In the first embodiment, the spring frame is selectively movable between deflected and undeflected configurations and comprises a flexible spring body having a distal end and a proximal end attached to the distal end of the catheter body. Positioned on the distal end of the spring body is a tip member. Additionally, disposed within the spring body are a plurality of strain relief slots for facilitating the deflection of the spring frame within a first deflection plane. The strain relief slots are formed in the spring body in a manner defining first and second continuous, longitudinally extending stiffening portions within the spring body which are oriented substantially diametrically opposite each other therewithin, and lie in a second plane perpendicular to the first deflection plane. The tip member is preferably formed as a separate piece which is attached to the distal end of the spring body via a weld or an adhesive, though it may alternatively be integrally formed on the distal end of the spring body.

In the first embodiment, the spring body includes at least 39 pairs of strain relief slots extending between the proximal and distal ends thereof which are preferably spaced within the spring body at intervals of approximately 0.015 to 0.031 inches. Each of the strain relief slots has a width proportional to the diameter of the spring frame and preferably 0.005+/−0.0005 inches, except for the strain relief slots of the three proximal most pairs which each have a width of a larger proportion to the diameter of the spring frame, and preferably 0.011+/−0.005 inches. Additionally, each of the strain relief slots other than those of the six proximal most pairs includes a stress relief end cutout portion to prevent cracking of the spring frame when deflected in the first deflection plane.

Extending longitudinally through the catheter body and the spring frame is a pair of activation wires having distal ends attached to the tip member in a manner wherein the wires extend through the spring body in an orientation substantially diametrically opposite each other and lying in the first deflection plane when the spring frame is in the undeflected configuration. Each of the activation wires of the pair are formed of stainless steel and have a diameter proportional to the diameter of the spring frame, and preferably not exceeding 0.007 inches. Additionally, the distal ends of the wires are preferably received into a pair of apertures disposed within the tip member and crimped to prevent the distal ends from sliding through the pair of apertures. Alternatively, the distal ends of the wires may be tied in a knot to prevent the same from sliding through the pair of apertures. Though the tip member preferably includes the aforementioned receiving apertures, such apertures need not be included, with the distal ends of the activation wires being welded directly to the tip member.

Encasing each of the activation wires within the spring body proximal the distal ends thereof is a pair of support sleeves. In the first embodiment, each of the support sleeves is attached to a proximal portion of the spring body in a manner operable to maintain the wires in the diametrically opposed orientation within the spring body and constrain the wires to move only in a longitudinal direction within the spring body. The distal ends of the pair of support sleeves are inserted into the proximal end of the spring body and extend therewithin to the first pair of relief slots including stress relief end cutout portions. Additionally, each of the support sleeves of the pair is attached to the spring frame via a mechanical method such as spot welds which are located between at least three of the six proximal most pairs of relief slots. Each of the support sleeves further defines an internal gap sized to closely encase a respective one of the activation wires, while allowing the wire to slide freely in the longitudinal direction within the spring body.

Encasing the spring body of the spring frame is an outer, flexible, thin-walled protective covering. The protective covering preferably comprises a flexible polymer sheath having a thin wall thickness, preferably not exceeding 0.0015, which is placed onto the spring body of the spring frame via various methods including but not limited to heat shrinking. Extending through the catheter body and the spring frame is at least one illumination fiber bundle for transmitting light through the endoscope. Also extending longitudinally through the catheter body and the spring frame is at least one image-transmitting fiber bundle as well as a working channel preferably having a diameter of at least 0.040 inches. The catheter body and spring frame may include a pair of image-transmitting fibers extending longitudinally therethrough for providing a stereo image. The catheter body preferably comprises a flexible, tubular frame formed of stainless spring steel having a downturned distal end and an outer jacket of plastic, i.e. PEBAX, disposed thereabout. Extending longitudinally through the catheter body and spring body is a flexible inner core extrusion. The catheter body is attached to the spring frame via the receipt of the downward distal end of the tubular frame into the proximal end of the spring body.

The bi-directional endoscope of the first embodiment is operated by stressing the activation wires by subjecting either of the wires to a tensile force. In this respect, stressing either of the activation wires is operable to transmit the tensile force from the stressed wire to the tip member, thus causing the spring frame to deflect in the first deflection plane toward the stressed wire. In the first embodiment, the proximal end of the catheter body is connected to a control assembly which comprises a main housing portion to which the proximal end of the catheter body is connected. Attached to the housing and cooperatively interfaced to one or more of the image-transmitting fibers is an eye piece. Additionally, pivotally connected to the housing is a handle member. The proximal ends of the actuation wires are engaged to the handle member in a manner wherein the selective pivotal movement of the handle member is operable to stress either of the activation wires in the aforementioned manner, thus causing the deflection of the spring frame in the first deflection plane.

In accordance with a second alternative embodiment of the present invention, there is provided a multi-directional endoscope. The spring frame of the multi-directional endoscope differs from the spring frame of the bi-directional endoscope previously described in that the relief slots are disposed within the spring body in a manner defining first, second and third continuous, longitudinally extending stiffening portions within the spring body which are equidistantly spaced at intervals of approximately 120 degrees therewithin. Additionally, the multi-directional endoscope includes three activation wires extending longitudinally through the catheter body and spring body which have distal ends attached to the tip member in a manner wherein each of the wires is disposed approximately halfway between a respective pair of the stiffening portions. The proximal ends of each of the three wires are engaged to the handle member of the control assembly. Due to the inclusion of three equidistantly spaced stiffening portions within the spring body and the three activation wires, the spring frame is deflectable in multiple directions and not confined to a single deflection plane. It is further contemplated that the spring frame may be fabricated having a single stiffening portion or greater than three stiffening portions, as well as one activation wire or greater than three activation wires.

BRIEF DESCRIPTION OF THE DRAWINGS

These, as well as other features of the present invention will become more apparent upon reference to the drawings wherein:

FIG. 1 is a perspective view of a bi-directional endoscope incorporating a spring frame constructed in accordance with a first alternative embodiment of the present invention;

FIG. 1a is a perspective view of the distal portion of the endoscope shown in FIG. 1 illustrating the bi-directional movement capability of the distal end;

FIG. 2 is a partial cutaway view of the distal portion of the endoscope illustrating a portion of the spring frame disposed therein;

FIG. 3 is a perspective view of the distal portion of the spring body of the spring frame;

FIG. 4 is a top plan view of the spring body;

FIG. 4a is a cross-sectional view through line A—A of FIG. 4.

FIG. 5 is a cross-sectional view of the distal portion of the spring frame;

FIG. 6 is a front elevational view of the spring frame shown in FIG. 5;

FIG. 7 is a cross-sectional view of the distal portion of a spring frame constructed in accordance with a second alternative embodiment of the present invention;

FIG. 8 is a cross-sectional view taken along line 8—8 of FIG. 7;

FIG. 9 is a cross-sectional view of a spring frame constructed in accordance with a third alternative embodiment of the present invention for use in conjunction with a multi-directional endoscope;

FIG. 10 is a cutaway perspective view of a handle member of the multi-directional endoscope, illustrating the engagement of the activation wires shown in FIG. 9 thereto;

FIG. 11 is a cross-sectional view of the spring frame of the third embodiment as engaged to the catheter body of the multi-directional endoscope;

DETAILED DESCRIPTION OF THE PREFERRED EMBODIMENT

Figure 12:
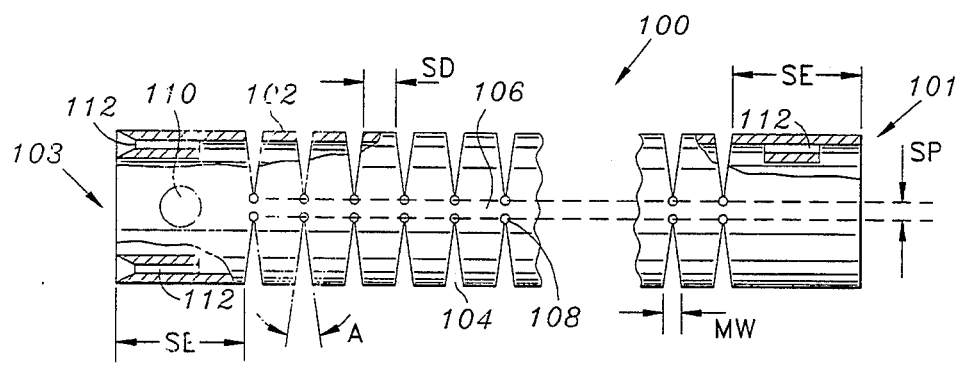
FIG. 12 is a top plan view of a spring body of a spring frame constructed in accordance with a fourth alternative embodiment of the present invention.

Referring now to the drawings wherein the showings are for purposes of illustrating preferred alternative embodiments of the device shown and described in U.S. patent application Ser. No. 07/818,670 of which the present application is a continuation-in-part, FIG. 1 perspectively illustrates a bi-directional endoscope 10 constructed in accordance with the present invention.

The endoscope 10 generally comprises an elongate, tubular catheter body 12 having a proximal end 14 and a distal end 16. The proximal end 14 of the catheter body 12 is connected to a control assembly 18. The control assembly 18 comprises a main housing portion 20 to which the proximal end 14 of the catheter body 12 is connected. Connected to the main housing portion 20 is an eye piece 22, the use of which will be discussed below. Additionally, pivotally connected to the housing 20 is a handle member 24 which is movable in the manner designated by the arrow in FIG. 1 for purposes of bi-directionally deflecting the distal portion of the catheter body 12 in the manner shown in FIG. 1a. The manner in which the handle member 24 is cooperatively engaged to the catheter body 12 to facilitate the bi-directional deflection of the distal portion thereof will be described more fully below.

Referring now to FIGS. 2-4, attached to and extending axially from the distal end 16 of the catheter body 12 is a generally cylindrical, tubular spring frame 26 which is selectively movable between deflected and undeflected configurations (as shown in FIG. 1a). In a first alternative embodiment of the present invention, the spring frame 26 comprises a flexible spring body 28 having a distal end 30 and a proximal end 32 which is attached to the distal end 16 of the catheter body 12. Disposed within the spring body 28 are a plurality of relief slots 34 which are adapted to allow the deflection of the spring frame 26 within a first deflection plane D1. The relief slots 34 are provided in pairs, and formed in the spring body 28 in a manner defining first and second continuous, longitudinally extending stiffening portions 36 within the spring body 28 which, as seen in FIG. 8, are oriented substantially diametrically opposite each other therewithin and lie in a second plane D2 perpendicular to the first deflection plane D1. As will be recognized, the opposed diametric orientation of the stiffening portions 36 facilitates the bi-directional movement capability of the spring frame 26 in the first deflection plane D1 in the manner shown in FIG. 1a.

In the first embodiment, the spring body 28 includes at least 39 pairs of the relief slots 34 between the proximal end 32 and distal end 30 thereof. As seen in FIG. 4, each of the relief slots 34 preferably has a width W1 which is proportional to diameter of spring frame, and in the embodiment shown, preferably 0.005+/−0.0005 inches except for each of the strain relief slots 34 of the three pairs disposed closest the proximal end 32 of the spring body 28 which each have a width W2 proportional to the diameter of spring frame, in them embodiment shown, and preferably 0.011+/−0.005 inches. Additionally, except for the relief slots 34 of the six proximal most pairs, each of the relief slots 34 includes a stress relief end cutout portion 38 to prevent cracking of the spring frame 26 when deflected in the first deflection plane D1. Each stress relief end cutout 38 preferably has a larger width W3, which is, in the embodiment shown approximately 0.011+/−0.001 inches.

As further seen in FIG. 4, each pair of relief slots 34 is preferably separated from an adjacent pair of relief slots 34 by a proportional distance S1 which, in the embodiment shown, is approximately 0.015+/−0.005 inches. Additionally, each of the stiffening portions 36 is preferably formed having a width W4, which is, in the embodiment shown, approximately 0.0065+/−0.0015 inches. However, as also seen in FIG. 4, the width of each of the stiffening portions 36 proximal to the proximal most pair of relief slots 34 including end cutouts 38 which, in the embodiment shown, preferably increases to a width W5 of approximately 0.020 inches +/−0.005 inches. Disposed within each of the stiffening portions 36 is an elongate slot 40 which extends longitudinally from the proximal end 32 of the spring body 28 and essentially bifurcates the portion of the stiffening portions 36 formed at the width W5. Each slot 40 preferably has a length of approximately 0.073+/−0.005 inches and a width of approximately 0.005+/−0.002 inches. However, the size is proportional to the size of the catheter, and may vary accordingly. The purpose for the inclusion of the slots 40 and providing the three proximal most pairs of relief slots 34 with the width W2 exceeding the width W1 will be explained below. As will be recognized, the aforementioned widths and spacings of the relief slots 34, end cutouts 38 and stiffening portions 36 are adapted to provide the spring body 28, and hence the spring frame 26, with optimal bi-directional deflection characteristics. However, it will be recognized that the configurations and dimensions associated with the relief slots 34, end cutouts 38 and stiffening portions 36 of the spring body 28 may be modified while still maintaining the bi-directional deflection characteristics thereof. The spring body 28 is preferably fabricated from stainless steel, though other materials may be utilized as an alternative. Additionally, the relief slots 34, end cutouts 38 and slots 40 are preferably formed within the spring body 28 via an electron discharge machining (EDM) process.

Formed about the distal end 30 of spring body 28 is an annular flange portion 42, which, in the embodiment shown, has a preferred overall diameter of approximately 0.083+/−0.001 inches and a width of approximately 0.050+/−0.005 inches. As seen in FIG. 5, positioned on the distal end 30 of the spring body 28, and more particularly the flange portion 42, is a tip member 44. Tip member 44 is formed to include a rounded head portion 46 having an annular portion 48 extending axially therefrom. Annular portion 48 is preferably sized having an inner diameter dimension substantially the same or slightly exceeding the outer diameter dimension of the flange portion 42 of the spring body 28. Tip member 44 is attached to the distal end 30 of the spring body 28 by sliding the same along the outer surface of the flange portion 42 until such time as the proximal most end of the annular portion 48 abuts a slight step 50 defined between the flange portion 42 and remainder of the spring body 28. In the first embodiment, the tip member 44 is secured to the flange portion 42 via a spot weld, though adhesives or other suitable affixing methods, or one piece construction may be utilized as an alternative. Additionally, the inner diameter dimension of the annular portion 48 and the outer diameter dimension of the flange portion 42 may be specifically sized such that the tip member 44 is frictionally retained upon the flange portion 42. Disposed within and extending longitudinally through the tip member 44 is a first bore 52, a second bore 54 having a diameter substantially less than the diameter of the first bore 52, and a plurality of third bores 56 having diameters slightly less than the diameter of the second bore 54. The use of the bores 52, 54 and 56 will be discussed below.

Extending longitudinally through the catheter body 12 and spring frame 26 are a pair of activation wires 58.

In the first embodiment, each of the activation wires 58 have distal ends which are attached to the tip member 44 in a manner wherein the wires 58 extend through the spring body 28 in an orientation substantially diametrically opposite each other and lying in the first deflection plane D1 when the spring frame 26 is in the undeflected configuration. Each of the activation wires 58 may be formed of any suitable material (e.g., metal, plastic, etc.,) and is preferably formed of stainless steel and has a diameter not exceeding approximately 0.007 inches. In the first embodiment, the activation wires 58 are attached to the tip member 44 via the receipt of the distal ends thereof into a pair of apertures 60 disposed within the head portion 46 of the tip member 44. In this respect, the distal ends of the activation wires 58 each include an enlarged head 62 which is received into and retained within a counterbore formed within a respective aperture 60, in the manner shown in FIG. 5. As an alternative to interfacing the wires 58 to the tip member 44 in the aforementioned manner, the distal ends of the wires 58 may be directly welded to the tip member 44 or affixed thereto by any other suitable means which maintains the wires 58 in the diametrically opposed orientation in the first deflection plane D1. Examples of other such affixation methods include crimping or knotting the distal ends of the wires to prevent the same from sliding through the apertures 60.

Encasing the activation wires 58 within the spring body 28 proximal the distal ends of the wires 58 is a pair of tubular support sleeves 64. Each of the support sleeves 64 is attached to a proximal portion of the spring body 28 in a manner operable to maintain the wires 58 in the diametrically opposed orientation within the spring body 28 and constrain the wires 58 to move only in a longitudinal direction within the spring body 28. As best seen in FIG. 7, the support sleeves 64 are received into the proximal end 32 of the spring body 28 and extend therewithin to the first pair of relief slots 34 including stress relief end cutouts 38. Each of the support sleeves 64 is attached to the spring body via spot welds SW which are included between the proximal most pair of relief slots 34 including end cutouts 38 and the next three successive pairs of relief slots 34 not including end cutouts 38. However, it will be recognized that the support sleeves 64 may be secured within the spring body 28 by any other alternative means which properly orients the support sleeves 64 in the aforementioned manner. As previously indicated, each of the support sleeves 64 has a generally tubular configuration and defines an internal gap sized to closely encase a respective one of the activation wires 58 while allowing the wire to slide freely in the longitudinal direction within the spring body 28. Importantly, the support sleeves 64 do not extend completely through the length of the spring frame 26 so as not to adversely affect the deflective capacity of the spring frame 26.

Optionally, to provide guidance and placement for the control wires at one or more points mid-way through the spring frame 26, one or more of the slotted segments of spring frame 26 may be indented at points 180° from one another such that the control wires may pass outboard of such spring segment(s), while remaining longitudinally advanceable and retractable relative to such spring segment. For example, as shown in FIGS. 4 and 4a, one slotted segment(s) positioned near the longitudinal mid-point of the spring frame 26 is provided with a first web or indentation or 39a and a second web or indentation 39b. Indentations 39a, 39b are positioned on opposite sides of the spring frame 28 such that the control wires 58 will pass outboard of the indentations 39a, 39b, while remaining unaffixed thereto, and freely longitudinally advanceable and retractable relative thereto. As such, the indentations 39a, 39b will serve to prevent inward movement and contact between the control wires 58 when such control wires 58 become slackened. It will be appreciated that, as an alternative to the indentations 39a, 39b shown in FIG. 4a, short segments of hypotube or other suitable tubing material may be affixed to the inner walls of one or more slotted segment(s) of the spring frame 28 such that control wires 58 pass through such segments of tubing while remaining laterally guided and retained thereby. Accordingly, internally mounted segments of tubing material may also serve as guide members for the control wires 58 at various points through the length of the spring frame body 28.

Referring now to FIG. 7, illustrated is a spring frame 26a which is a modification of the spring frame 26 previously discussed. Spring frame 26a comprises a spring body 28a which is identical to the spring body 28 except that the spring body 28a includes a tip portion 44a integrally formed on the distal end thereof as opposed to comprising a separate piece which is attached to the distal end of the spring body 28a. As also seen in FIG. 7, the distal ends of the activation wires 58 extending through the spring frame 26a and into the apertures 60a disposed in the tip portion 44a thereof are crimped to secure the same to the tip portion 44a. Though mechanical means, such as spot welds, SW are illustrated as securing the support sleeves 64 to the spring body 28a, as previously discussed, such spot welds SW are also utilized to secure the support sleeves 64 to the spring body 28 of the spring frame 26.

Encasing the spring body 28, 28a of the spring frame 26, 26a is an outer, flexible, thin-walled protective covering 66. In the first and second alternative embodiments, the protective covering 66 comprises a flexible polymer sheath having a wall thickness not exceeding approximately 0.0015 inches. Additionally, the covering 66 is preferably heat shrunk onto the spring body 28, 28a of the spring frame 26, 26a. As seen in FIG. 5, the outer diameter of the annular portion 48 of the tip member 44 is sized such that when the protective covering 66 is disposed about the spring body 28, the outer surface of the protective covering 66 and the outer surface of the annular portion 48 are substantially continuous. Similarly, as seen in FIG. 7, the outer diameter of the tip portion 44a is sized such that when the protective covering 66 is disposed about the spring body 28a, the outer surface of the protective covering 66 and the outer surface of the tip portion 44a are also substantially continuous. Additionally, as seen in FIGS. 1a and 2, the protective covering 66 is preferably sized so as to extend proximally to a length sufficient to overlap the distal end 16 of the catheter body 12.

Referring now to FIG. 9, cross-sectionally illustrated is a spring frame 70 constructed in accordance with a third alternative embodiment of the present invention for use in a multi-directional endoscope. In the third embodiment, spring frame 70 includes a spring body 72 which is similar to the spring body 28, except that the relief spots are disposed within the spring body 72 in a manner defining three stiffening portions 74. As seen in FIG. 9, the stiffening portions 74 are equidistantly spaced about the periphery of the spring body 72 and separated by approximately 120 degrees. Advantageously, by providing the spring body 72 with the three stiffening portions 74, the spring frame 70 is not limited to deflection within a single deflection plane, but rather is deflectable in multiple deflection planes.

To facilitate the multi-directional deflection of the spring frame 70, extending longitudinally through the spring frame 70 are three activation wires 76. Each of the activation wires 76 is preferably centrally disposed between a respective pair of the stiffening portions 74 and includes a distal end which is secured to a tip member attached to the distal end of the spring body 72 in the same manner previously discussed with respect to the first and second embodiments. Encasing the activation wires 76 within the spring body 72 proximal the distal ends of the wires 76 are support sleeves 78. The support sleeves 78 are received into the proximal end of the spring body 72 and extend therewithin and are secured thereto in the same manner previously discussed with respect to the support sleeves 64 and spring bodies 28, 28a. Like the spring frames 26, 26a, the spring frame 70 is attached to and extends axially from the distal end of the catheter body 12 of the multi-directional endoscope, with the spring body 72 being encased by a protective covering which extends proximally a distance sufficient to overlap the distal end of the catheter body.

Referring now to FIG. 10, the multi-directional endoscope includes a control assembly 18a which is substantially identical to the control assembly 18 previously described with respect to the bi-directional endoscope 10. To facilitate the multi-directional movement of the spring frame 70, the proximal ends of each of the three activation wires 76 are attached to the ball portion 80 of the handle member 24a pivotally interfaced to the housing portion 20a of the control assembly 18a. Though not shown, the proximal ends of the two activation wires 58 previously described are interfaced to a ball portion of the handle member 24 of the control assembly 18 in a similar manner to facilitate the bi-directional movement of the spring frame 26 as shown in FIG. 1a. However, since the spring frame 26 is movable only in the first deflection plane D1, the handle member 24 is only pivotal in the direction designated by the arrow in FIG. 1.

In the first embodiment of the present invention, the spring frame 26 of the bi-directional endoscope 10 is selectively deflected within the first deflection plane D1 by manipulating the handle member 24 so as to stress one of the activation wires 58. In this respect, the activation wires 58 are stressed by subjecting either of the wires 58 to a tensile force. In operation, the tensile force is transmitted from the stressed wire to the tip member 44 or tip portion 44a, thus causing the spring body 28, 28a to deflect in the deflection plane D1 toward the stressed wire. The multi-directional endoscope operates in a similar manner in that the spring body 72 also deflects toward the stressed wire or wires when the handle member 24a is manipulated. However, due to the incorporation of the three activation wires 76, pairs of the wires may be simultaneously stressed to varying degrees, thus facilitating the deflection of the spring frame 70 in more than one deflection plane. Though not shown, it is further contemplated that spring frames may be fabricated in accordance with the present invention wherein the spring bodies incorporate a single stiffening portion, or four or more stiffening portions to achieve varying amounts of deflective capacity.

The bi-directional and multi-directional endoscopes of the present invention each include at least one illumination fiber bundle 82 extending through the catheter body and the spring frame 26, 70 for transmitting light therethrough. Also extending longitudinally through the catheter body and spring frame 26, 70 is at least one image-transmitting fiber bundle 84. As seen in FIG. 11, the multi-directional endoscope incorporates a pair of image-transmitting fibers 84 for providing the multi-directional endoscope with stereo-imaging capability. It will be recognized that the bi-directional 10 may also be provided with a pair of image-transmitting fibers 84 for providing such stereo imaging.

The catheter body 12 of the bi-directional endoscope 10 and catheter body of the multi-directional endoscope preferably comprises a flexible, tubular frame preferably formed of a stainless spring steel wire having a downturned distal end and an outer jacket formed of plastic (and preferably PEBAX) disposed thereabout. As seen in FIG. 11, the tubular frame of the multi-directional endoscope includes an inner core extrusion 86 extending longitudinally therethrough which defines apertures adapted to receive and accommodate the image-transmitting fibers 84 and illumination fibers 82. The inner core extrusion 86 further includes three recesses 88 formed within and extending longitudinally along the outer surface thereof which are adapted to accommodate the support sleeves 78. Also extending longitudinally therethrough is a working lumen 90 having an inner diameter of at least 0.040 inches. Advantageously, the inner core extrusion 86 is sized so as to be extensible through both the catheter body and spring frame 70. Additionally, the inner core extrusion 86 is fabricated from a material possessing sufficient resiliency to allow the inner core extrusion 86 to bend with the spring frame 70. In the multi-directional endoscope, the catheter body is attached to the spring frame 70 via the receipt of the downturned distal end of the tubular frame into the proximal end of the spring body 72. After being received into the proximal end of the spring body 72, the distal end of the tubular frame is retained therein via an adhesive or any other suitable fastening means. Alternatively, the outer diameter of the downturned distal end may be sized to exceed the inner diameter of the spring body 72 such that the distal end may be frictionally retained therewithin.

Though not shown, it will be recognized that the inner core extrusion used in conjunction with the catheter body 12 is substantially similar to the inner core extrusion 86, except that only two recesses 88 will be included therein in an orientation adapted to accommodate the support sleeves 64. The inner core extrusion used in conjunction with the catheter body 12 is extended through the tubular frame of the catheter body 12 and spring frame 26, 26a. Importantly, the inner core extrusion is advanced through the spring body 28, 28a to the head portion 46, 46a of the tip 44, 44a, such that the working lumen thereof is coaxially aligned with the first bore 52, with the image transmitting fiber being coaxially aligned with the second bore 54 and the illumination fibers being coaxially aligned with the third bores 56. The catheter body 12 is attached to the spring frame 26, 26a via the receipt of the downturned distal end of the tubular frame of the catheter body 12 into the proximal end 32 of the spring body 28, 28a. When inserted into the proximal end 32, the downturned distal end extends within the spring body 28, 28a to the distal most one of the three pairs of relief slots 34 having the width W2. Though the downturned distal end of the tubular frame may be adhesively secured to the proximal end of the spring body 28, 28a, it is preferably sized in the aforementioned manner to be frictionally retained therein. In this regard, the slots 40 and the three proximal most pairs of relief slots 34 having the width W2 are provided to allow a slight expansion of the proximal end 32 of the spring body 28, 28a to accommodate the larger diameter distal end.

Referring now to FIGS. 12-15, illustrated are alternative embodiments of the spring frame which may be utilized in conjunction with either the bi-directional endoscope 10 or multi-directional endoscope as an alternative to the spring frames 26, 26a and 70, as well as the one stiffening portion and four stiffening portion spring frames previously described. In accordance with a fourth alternative amendment, there is provided a spring frame 100 comprising a spring body 102 which has a proximal end 101, a distal end 103 and includes a plurality of relief slots 104 disposed therein. The relief slots 104 are provided in pairs which are disposed along the length of the spring body 102 between the proximal 101 and distal end 103 thereof in a manner defining at least one stiffening portion 106, though it will be recognized that such relief slots 104 may be formed so as to define two or more stiffening portions. In the fourth embodiment shown in FIG. 12, the spring body 102 preferably has an outer diameter of approximately 0.084 inches and includes at least 20 pairs of the relief slots 104 disposed between the proximal end 101 and distal end 103 thereof. Additionally, each of the relief slots 104 includes a generally circular stress relief end cutout 108 to prevent cracking of the spring frame 100 when such is deflected. To further reduce stress, provided adjacent the distal end 103 of the spring body 102 is a keyhole 110 preferably having a diameter of approximately 0.020+/−0.005 inches.

In the spring body 102, each of the relief slots 104 is preferably formed at an angle A of approximately 10 degrees and has a maximum width MW of approximately 0.0073+/−0.005 inches. Additionally, each of the end cutouts 108 is preferably formed having a radius of approximately 0.00025 inches. As also seen in FIG. 12, each pair of relief slots 104 is preferably separated from an adjacent pair of the relief slots 104 by a distance SD of approximately 0.024+/−0.005 inches, with the at least one stiffening portion 106 defined by the relief slots 104 having a width SP of approximately 0.0050 inches. The distances SE separating the proximal most pair of relief slots 104 from the proximal end 101 and the distal most pair of relief slots 104 from the distal end 103 are preferably identical and approximately 0.060+/−0.005 inches. Advantageously, the spring body 102 of the spring frame 100 is also formed in a manner defining a number of internal channels 112 which are adapted to accommodate the activation wires extending longitudinally through the spring frame 100. Though not shown, in constructing the spring frame 100, a tip member like the tip member 44 previously described is attached to the distal end 103 of the spring body 102.

Figure 13:
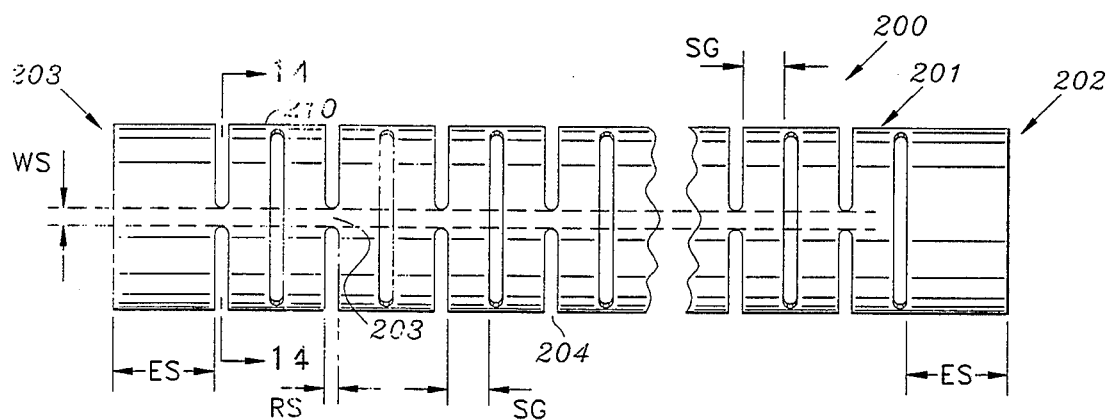
FIG. 13 is a top plan view of a spring body of a spring frame constructed in accordance with a fifth alternative embodiment of the present invention.
Figure 14:
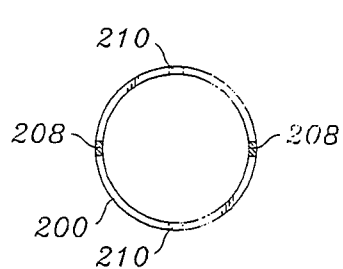
FIG. 14 is a cross-sectional view taken along line 14—14 of FIG. 13.
Figure 15:
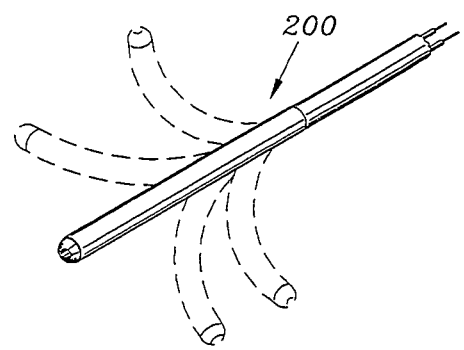
FIG. 15 is a perspective view of the distal portion of an endoscope incorporating the spring body shown in FIGS. 13 and 14, illustrating the multi-directional movement capability of the distal end of the catheter body.

As seen in FIGS. 14 and 15, illustrated is a spring frame 200 constructed in accordance with a fifth alternative embodiment of the present invention. Spring frame 200 comprises a spring body 201 having a proximal end 202, a distal end 203 and an outer diameter of approximately 0.087 inches. Disposed between the proximal end 202 and distal end 203 of the spring body 201 are a plurality of relief slots 204 which are included in pairs along the length of the spring body 201. Disposed between adjacent pairs of the relief slots 204 are elongate relief grooves 206. As seen in FIG. 13, the spring body 201 is formed in a manner wherein a pair of relief slots 204 is formed closest the distal end 203, while a relief groove 206 is formed closest the proximal end 202. In the fifth embodiment, 20 pairs of relief slots 204 and 20 relief grooves 206 are formed along the length of the spring body 201.

In the spring body 201, each of the relief slots 204 preferably has a width RS of approximately 0.005 inches, while each of the relief grooves 206 preferably has a width RG of approximately 0.005 inches. Additionally, the preferred distance SG separating each pair of relief slots 204 from each relief groove 206 is approximately 0.015+/−0.005 inches. As also seen in FIG. 13, the distances ES separating the distal most pair of relief slots 204 from the distal end 203 and the proximal most relief groove 206 from the proximal end 202 are preferably identical and approximately 0.035+/−0.005 inches.

Unlike the spring bodies 28, 28a, 70 and 100 previously described, the incorporation of the intermittent pairs of relief slots 204 and relief grooves 206 in the spring body 201 does not create a continuous stiffening portion, but rather defines diametrically opposed pairs of longitudinally aligned stiffening segments 208, each of which are separated by a relief groove 206. The preferred width WS of each of the stiffening segments 208 is approximately 0.005+/−0.002 inches.

As seen in FIG. 14, the relief grooves 206 do not extend completely through the spring body 201, thus forming a second diametrically opposed pair of stiffening segments 210 which lie on a plane perpendicular to the plane on which the stiffening segments 208 lie. Advantageously, this configuration allows the spring frame 200 to be deflected in the manner shown in FIG. 15. It will be recognized that both the spring body 201 is also adapted to have tip members such as the tip member 44 attached to the distal end 203 thereof.

Additional modifications and improvements of the present invention may also be apparent to those skilled in the art. For example, it will be recognized that the particular dimensions set forth in the description pertain to the specific embodiments shown in the drawings, and that certain proportions, ratios or different dimensions may be substituted therefor to provide the desired performance characteristics of the device. Thus, the particular combination of parts described and illustrated herein is intended to represent only one embodiment of the invention, and is not intended to serve as limitations of alternative devices within the spirit and scope of the invention.

What is claimed is:

1. A guidable catheter for insertion in a mammalian body, said device comprising:
 (a) a flexible catheter sheath having a distal end, a proximal end and at least one lumen extending longitudinally therethrough;
 (b) a bending assembly positioned on the distal end of said catheter sheath, said bending assembly comprising:
  i. a tubular spring frame having a longitudinal axis, proximal and distal ends, and a hollow bore extending longitudinally therethrough;
  ii. at least one first series of substantially parallel relief slots cut partway through said tubular spring frame perpendicular to the longitudinal axis thereof, each of said relief slots being of a first width having end cutout regions on either end thereof, said end cut out regions being of a second width which is greater than said first width;

iii. said relief slots being sized and located relative to one another so as to render said tubular spring frame bendable in at least one lateral direction;

(c) at least one tension wire extending longitudinally through said catheter sheath and through the bore of said tubular spring frame, said tension wire being connected to said tubular spring frame near the distal end thereof, said tension wire being controllable from the proximal end of said catheter sheath such that retraction of said tension wire in the proximal direction will cause said tubular spring frame to bend in a lateral direction and subsequent relaxation of said tension wire will allow said tubular spring frame to return to a straight non-bent configuration.

2. The catheter device of claim 1 wherein said catheter device comprises an endoscope and wherein said endoscope further comprises:

at least one light transmitting pathway extending longitudinally through said catheter sheath and through the bore of said tubular spring frame to transmit illuminating light from a light source, through said catheter device, to the distal end of said tubular spring frame;

at least one optical image transmitting pathway extending from the distal end of said tubular spring frame, through the bore of said tubular spring frame and through said catheter sheath, said optical image transmitting pathway being coupleable to an image viewing apparatus positioned near the proximal end of said catheter sheath to receive and display an optical image received through said optical image transmitting pathway from the distal end of said tubular spring frame.

3. The catheter device of claim 1 wherein said bending assembly further comprises:

iv. at least one tubular column support member extending longitudinally through at least a portion of the bore of said tubular spring frame and being anchored to a side of said tubular spring frame, each said tubular column support member surrounding a segment of a tension wire extending through said tubular spring frame to hold said tension wire along one side of said tubular spring frame while allowing said tension wire to remain longitudinally moveable therethrough.

4. The device of claim 3 wherein said tubular column support member comprises a segment of hypodermic needle tubing.

5. The device of claim 1 wherein the first width of each of said relief slots in said first series is approximately 0.0045–0.0055 inches.

6. The device of claim 5 wherein the second width of each of said end cutout regions of each of said relief slots is approximately 0.010–0.012 inches.

7. The device of claim 1 wherein the bending assembly further comprises:

a second series of substantially parallel relief slots cut partway through said tubular spring frame perpendicular to the longitudinal axis thereof, said relief slots of said second series having a third width which differs from the first width of the relief slots of said first series.

8. The device of claim 1 wherein said at least one first series of release slots comprises a single series of release slots cut more than halfway through the tubular spring frame such that a single longitudinal strip of the spring frame remains uncut and forms a single stiffening portion along one side of the spring frame.

9. The device of claim 1 wherein said at least one first series of relief slots comprises a left first series of slots cut less than halfway through the spring frame body on one side thereof, and a right first series of slots cut less than halfway through the spring frame body on the opposite side thereof, such that two (2) longitudinal strips of the spring frame remain uncut, so as to form two (2) longitudinal stiffening portions on opposite sides of the spring frame body.

10. The device of claim 9 wherein said at least one tension wire comprises first and second tension wires, said first tension wire being connected to the side of said spring frame wherein said left first series of relief slots is formed and said second tension wire being connected to the side of said spring frame wherein said right first series of relief slots is formed, said catheter device being thereby alternately bendable in a first lateral direction upon proximal retraction of said first tension wire, and in a second lateral direction upon retraction of said second tension wire.

11. The device of claim 1 further comprising:

a distal tip member on the distal end of said tubular spring frame.

12. The device of claim 11 wherein said at least one tension wire extends fully through said tubular spring frame and is connected to a lateral side of said distal tip member such that proximal retraction of said tension wire will exert proximal draw on a lateral side of said distal tip member, thereby causing said spring frame to bend in a corresponding lateral direction.

* * * * *